US 6,533,453 B1

(12) United States Patent
Heidsieck et al.

(10) Patent No.: US 6,533,453 B1
(45) Date of Patent: *Mar. 18, 2003

(54) SYSTEM FOR LOCATING CASSETTES FOR PRODUCING DIGITAL IMAGES

(75) Inventors: Robert Heidsieck, Rocquencourt (FR); Vincent Rit, Douai (FR); Catherine Picard, Boulogne (FR); Jean Louis Baudet, Paris (FR)

(73) Assignee: GE Medical Systems SA (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/284,168
(22) PCT Filed: Oct. 3, 1997
(86) PCT No.: PCT/FR97/01745
§ 371 (c)(1), (2), (4) Date: Jun. 14, 1999
(87) PCT Pub. No.: WO98/15848
PCT Pub. Date: Apr. 16, 1998

(30) Foreign Application Priority Data

Oct. 10, 1996 (FR) .............................. 96 12381

(51) Int. Cl.⁷ ................................................ H05G 1/64
(52) U.S. Cl. ...................................................... 378/189
(58) Field of Search ........................... 378/32, 114, 115, 378/116, 182, 189, 204, 205, 207; 250/255.89

(56) References Cited

U.S. PATENT DOCUMENTS

| 4,070,582 | A |   | 1/1978  | Kisron .......................... 250/475 |
| 5,349,628 | A | * | 9/1994  | Taniguruma et al. ........ 378/181 |
| 5,661,309 | A | * | 8/1997  | Jeromin et al. .............. 250/580 |
| 5,844,961 | A | * | 12/1998 | McEvoy et al. ............. 378/98.8 |
| 5,883,937 | A | * | 3/1999  | Schmitt ........................ 378/189 |
| 6,102,866 | A | * | 8/2000  | Nields et al. ................. 600/461 |
| 6,296,386 | B1| * | 10/2001 | Heidsieck et al. ........... 378/189 |

FOREIGN PATENT DOCUMENTS

| DE | 3609527 | 5/1987 |
| EP | 0603709 | 6/1994 |
| EP | 0714038 | 6/1996 |

* cited by examiner

Primary Examiner—Drew A. Dunn
Assistant Examiner—Allen C. Ho
(74) Attorney, Agent, or Firm—Jay L. Chaskin

(57) ABSTRACT

System for locating cassettes for producing digital images, in a radiography apparatus of the type comprising an X-ray source, means for data processing, a support for the cassette in an active position and a storage space for the cassette in the inactive position. The cassette comprises means for detecting the insertion of the cassette into the support and means for detecting the identification of the cassette.

23 Claims, 3 Drawing Sheets

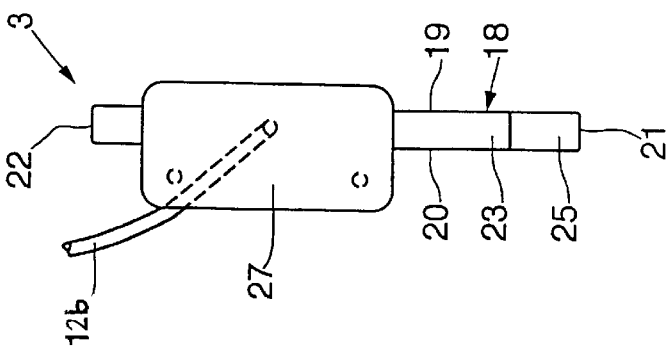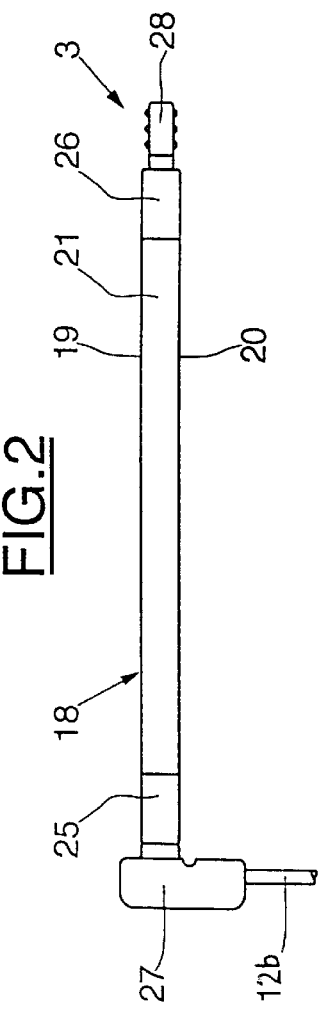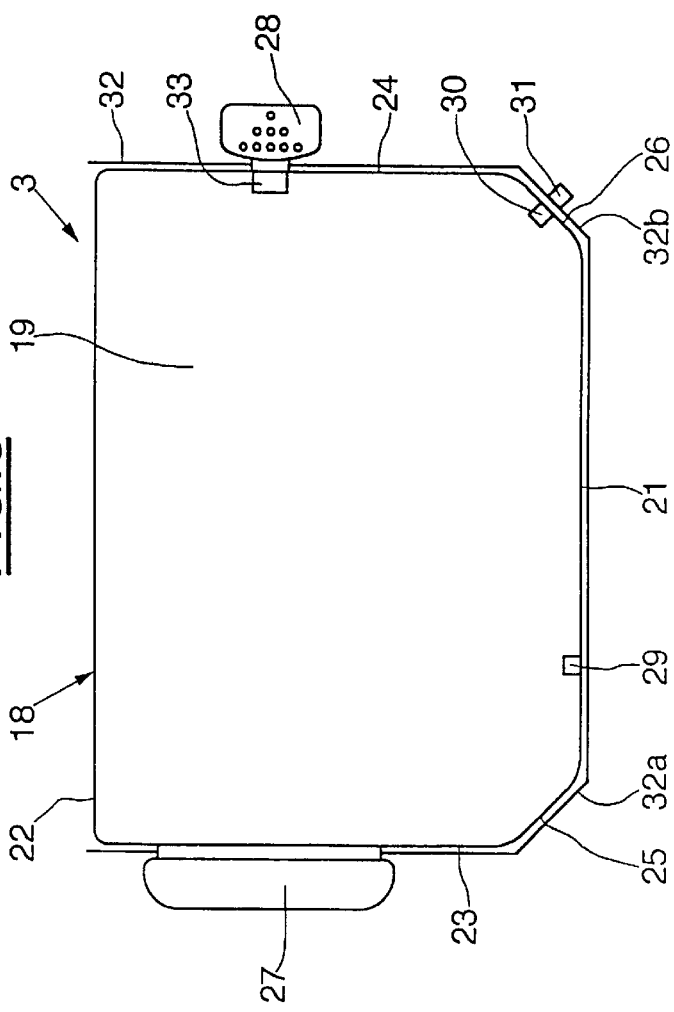

SYSTEM FOR LOCATING CASSETTES FOR PRODUCING DIGITAL IMAGES

CROSS-REFERENCE TO RELATED APPLICATIONS

This application claims the benefit of a priority under 35 USC 119 to French Patent Application No. 96 12381 filed Oct. 10, 1996 and PCT/FR97/01745 filed Oct. 3, 1997, the entire contents of which are incorporated by reference.

BACKGROUND OF THE INVENTION

The subject of the present invention is a system for locating cassettes for producing digital images for a radiography apparatus. In general, such radiography apparatuses comprise an X-ray emitter, a device for supporting the cassette for producing images, the organ to be radiographed being arranged between the X-ray emitter and the cassette support device, a means for processing the data thus obtained and a space for storing the cassette when it is not being used.

By way of example, there are known mammography apparatuses which comprise an X-ray source arranged on one side of the organ to be radiographed, a support table, transparent to X-rays, arranged on the other side of the organ to be radiographed, an adjustable holding plate which presses the organ onto the support table, and a housing for receiving a cassette for producing images containing an exposable film. The housing is arranged in the support table.

After an image of the organ has been produced, the cassette containing the exposed film is extracted from its housing, and the film is developed.

Such apparatuses are generally used for finding the possible symptoms of breast cancer. A first operation consists in carrying out systematic screening, which merely requires one or two frames to be taken. If these frames reveal the symptoms of cancer, more in-depth diagnosis is then carried out, which requires a larger number of frames, for example of a particular region of the organ, with a view to altering the way in which the images are represented and displayed. If the diagnosis reveals the presence of cancer, it may be necessary to perform a biopsy. A puncture system is then arranged on the radiology apparatus. The puncture system generally comprises a needle for taking a sample from a region suspected of being cancerous, for the purposes of analysis, and a needle holder. The radiology apparatus is then used for positioning the needle. The puncture system may also be used for inserting a hook equipped with a line intended for the surgeon to locate a cancerous region during an operation.

When the puncture system is used, a first frame is generally taken for centring the region to be punctured. After this, using a mechanism for tilting the X-ray source, one frame is taken at an angle of +15° and a second frame is taken at an angle of −15°, with the aim of obtaining the three-dimensional co-ordinates of a point of particular interest by stereotaxis. After the needle has been inserted into the organ, at least two control frames are taken to check that the needle is in place in the region to be punctured. In practice, a total of about eight frames is reached when using the puncture system. The development of an exposable film lasts 3 to 5 minutes per frame.

Throughout the biopsy operation and the development of the frames, the organ remains perfectly immobilized relative to the radiology apparatus, and is held in compression between the table and the holding plate. The patient must therefore remain more than 30 minutes in a stationary and relatively painful position.

With the aim of reducing the time for which the organ is immobilized, the cassettes containing exposable films may be replaced by cassettes containing a means for producing digital images, capable of producing images extremely quickly. The biopsy operations are thus much shorter and reduce the discomfort of these examinations. Furthermore, cassettes for producing digital images allow the quality of the diagnosis to be improved. For economic reasons, it is desirable to use cassettes for producing digital images without changing the rest of the radiology apparatus. The cassette should be removable, so that it can be arranged either under the table, during diagnosis, or in the puncture system, during a biopsy.

A cassette for producing digital images comprises a casing, within which device for detecting the radiographic signal is arranged. This detection device may, for example, comprise a scintillator capable of converting the incident X-rays into light radiation, an optical fibre making it possible to filter most of the X-radiation which has passed through the scintillator, and protecting the components located downstream of the said optical fibre, and a charge-coupled device (CCD) array camera forming a sensitive region. In order to ensure that the cassette is positioned appropriately in the housing, the cassette is generally provided with a locking means. The cassette is also provided with an electrical cable connecting it to a data processing means, in general a microcomputer.

If the cassette is inserted into a housing in an incorrect position or without the locking means being locked, there is a risk that this will compromise the quality of the images. It may prove necessary for the microcomputer to perform different image-processing routines, using appropriate software, depending on whether the cassette is being used in the puncture system or in the housing of the support table.

BRIEF DESCRIPTION OF THE INVENTION

The present invention is directed to a cassette location system which makes it possible to check that the cassette is positioned and locked suitably in its housing and to locate the cassette in the housing of the support table, in the puncture system or else in an inactive position.

The location system in an embodiment of the invention is intended for cassettes for producing digital images, in a radiography apparatus of the type comprising an X-ray source, a data processing means, a support for the cassette in the active position and a storage space for the cassette in the inactive position. The cassette comprises a means for detecting the insertion of the cassette into the support and a means for detecting the identification of the cassette. It is thus possible to recognize the type of cassette used as well as the position that the cassette occupies.

In one embodiment of the invention, the data processing means comprises a means for processing the digital signals output by the cassette, and a means for controlling the X-ray source.

In one embodiment of the invention, the system comprises a means for preventing the introduction of a cassette of standard parallelepipedal format into the storage space, the housing for the cassette in the storage space being provided with truncated corners, and the cassette whose introduction is allowed being of parallelepipedal format with truncated coners. This avoids conventional types of cassettes being introduced into the storage space of a radiology apparatus equipped with the location system.

Advantageously, the cassette comprises a detector for detecting insertion into the support, which is in the form of a mechanical relay.

In one embodiment of the invention, the cassette comprises a detector for identification in the storage space, which is in the form of a relay magnetically triggered by a magnet fitted to the storage space. In one embodiment of the invention, the cassette comprises a lock for immobilization in the support, a locking detector which is in the form of an electrical contact connecting to the support, and a means for digitizing the signal from the locking detector in order to send the locking data to the data processing means.

In one embodiment of the invention, the system furthermore comprises a puncture device capable of performing a biopsy and comprising a second support for the cassette in the active position. The second support may comprise a means for preventing the introduction of cassettes of standard parallelepipedal format, the housing for the cassette in the second support being provided with truncated corners, and the cassettes whose introduction is allowed being of parallelepipedal format with truncated corners. The cassette may comprise an insertion detector and an identification detector relating to the second support, which are in the form of a mechanical relay and a relay magnetically triggered by a magnet fitted to the second support.

Advantageously, the cassette comprises a lock for immobilization in the second support, a locking detector which is in the form of an electrical contact connecting to the second support, and a means for digitizing the signal from the locking detector in order to send locking data to the data processing means.

In one embodiment of the invention, the cassette is equipped with cables for transmission to the data processing means and comprises a handle intended for the cassette to be gripped and for the exit of the cable from the cassette to be protected.

By virtue of the invention, the operator immediately knows where the cassette he is looking for is located, and furthermore avoids any use of the cassette if the locking is defective or the positioning in a support is incorrect.

BRIEF DESCRIPTION OF THE DRAWINGS

The invention will be more clearly understood on studying the detailed description of embodiments, taken by way of entirely non-limiting examples and illustrated by the appended drawings in which:

FIG. 2 is a front elevation view of an embodiment of the cassette for producing images;

FIG. 3 is a top elevation view of an embodiment of the cassette for producing images;

FIG. 4 is a side elevation view of an embodiment of the cassette for producing images;

DETAILED DESCRIPTION OF THE INVENTION

Figure 1:
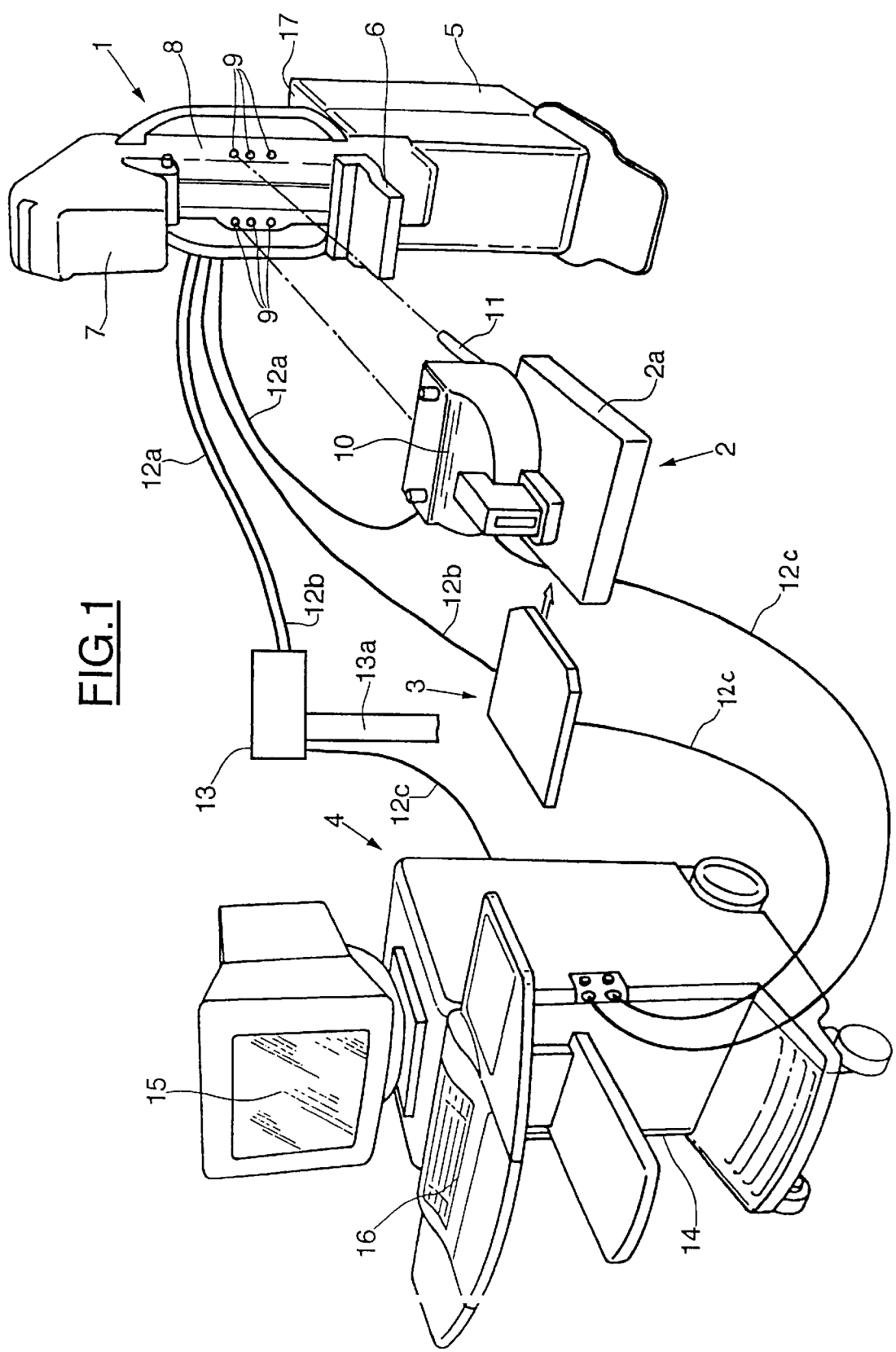
FIG. 1 is an overall perspective view of the radiology system.

As illustrated in the figures, the mammography system comprises a mammograph 1, a puncture system 2, a cassette 3, for producing digital images and a control and processing means 4. The radiology apparatus comprises a base 5, resting on the floor and supporting a breast support plate 6, also referred to as a "bucky, whose height can be adjusted, and an X-ray source 7 which can be tilted by +30° with respect to the vertical plane of symmetry of the radiology apparatus 1. The X-ray source 7 is supported by a column 8 whose front face is provided with a plurality of holes 9 for fastening the puncture system 2.

The puncture system 2 may optionally be mounted on the mammograph 1 and comprises a holding plate 2a acting as a compression pad, a needle holder 10 and a needle (not represented) capable of performing a biopsy in the organ to be radiographed. The puncture system 2 is equipped with two pins 11, only one of which can be seen in FIG. 1, which can be housed in the holes 9 in the column 8 of the mammograph 1, and with ball joints (not represented) for fastening on the column 8. The puncture system 2 is connected to a connection box 13 by an electrical cable 12a.

The cassette 3 for producing digital images is flat and substantially parallelepipedal with truncated coners, and is connected to the connection box 13 by an electrical cable 12b.

This connection box 13 is connected to the control and processing means 4 and comprises a start and stop button, the general supply of the system and the required data links (not represented). The connection box 13 may be mounted on a column 13a in which the excess lengths of cables are stored. The cables 12a and 12b pass through the mammograph 1 so as to limit the radius of movement of the cassette 3 and of the puncture system 2. This reduces the risks of the latter items being stored incorrectly.

The control and processing means 4 comprises a chassis 14 and electronic means (not represented), of the microcomputer type, which are connected to the puncture system 2 and to the cassette 3 by the electrical cable 12c, the connection box 13 and the electrical cables 12a and 12b for processing the data received from the cassette 3 and for controlling the puncture system 2, in particular the movement of the needle holder 10 during a biopsy. The control and processing means 4 can control the X-ray source 7 and also comprises a screen 15 for displaying the images of the radiographed organ and a keyboard 16. The control and processing means 4 may be equipped with software intended for calculating the three-dimensional co-ordinates of points in the radiographed organ on the basis of two images produced at different angles by virtue of the pivoting of the X-ray source 7. It is thus possible to obtain excellent visualization either of particular regions in the radio-graphed organ during diagnosis, or of the positioning of the needle in the radiographed organ during a biopsy, by using optimized display methods.

The cassette 3 may be inserted, along the direction of the arrow in FIG. 1, into a housing in the puncture system 2, or into a housing provided in a cassette holder (not represented) used during diagnostic examinations and intended to be fixed on the breast support plate 6, or alternatively, in the inactive position, into a storage space 17 on the mammograph 1.

In a manner which is not represented, the cassette 3 comprises a sensitive region with an upper wall, transparent to X-rays, a scintillator capable of converting the X-rays into visible light, a fibre-optic layer intended for forwarding the visible light, and an array camera composed of a plurality of charge-coupled cells (CCDs)

During operation, the X-rays are emitted by the source 7, pass through a holding plate (not represented), the radiographed organ, the breast support plate 6 and the upper wall of the sensitive region of the cassette 3, and enter the scintillator which, on receiving X-rays, emits visible light which is forwarded to the array camera by the fibre-optic layer. The array camera makes it possible to convert the information received in the form of visible light into information in the form of a digital electrical signal, which is transmitted by the electrical cables 12b and 12c to the control and processing means 4.

As can be seen in FIGS. 2 to 4, the cassette 3 comprises a substantially parallelepipedal case 18 comprising an upper face 19, a lower face 20, two longitudinal edges 21 and 22 and two side edges 23 and 24. Two truncated corners 25 and 26, both perpendicular to the upper face 19 and to the lower face 20, are respectively formed at the intersections between the longitudinal edge 21 and the side edge 23, and between the longitudinal edge 21 and the side edge 24. On the side edge 23 of the case 18 of the cassette 3, a handle 27 is arranged, used both for the operator to grip the cassette 3 and for protecting the electrical cable 12b where it leaves the case 18, in order to prevent a movement of the cable 12b relative to the case 18 from causing damage to the electrical contacts of the end of the cable 12b inside the case 18. Nevertheless, the handle 27 is kept small so as not to cause discomfort to the patient during the examination. On the side edge 24 opposite the side edge 23, the cassette 3 comprises a lock 28 for immobilizing the cassette 3 in its housing provided either in the breast support plate 6, the positioning system 2 or the storage space 17 (FIG. 1).

On its longitudinal edge 21, the cassette 3 comprises a detector 29 for detecting the insertion of the cassette 3 into the housing in the puncture system 2 or breast support plate 6. The detector 29 is in general of mechanical type with a plunger. It is thus possible to provide an electromechanical relay triggered by a tripper provided in the housings in the puncture system 2 and in the breast support plate 6. On its truncated comer 26, the cassette 3 also comprises a detector 30 for identification of the cassette 3, which is generally in the form of a magnetically triggered relay capable of being triggered by a magnet 31, fitted to the housing in the puncture system 2 and in the storage space 17, a contour 32 of which is schematically represented in FIG. 3.

The shape of the contour 32 of the housing is designed for receiving the cassette 3 and comprises truncated coners 32a and 32b corresponding to the truncated coners 25 and 26 of the cassette 3. The existence of the truncated coners 32a and 32b of the contour 32 of the housing prevents complete insertion of a conventional type of cassette into a housing intended for a cassette 18 according to the invention. If an operator tries to introduce a conventional type of cassette into such a housing, the square coners of the cassette will abut against the truncated coners 32a and 32b of the contour 32 of the housing and will prevent this cassette from being fully inserted into the housing. The operator will immediately realize the reason why insertion has failed and will then use the appropriate type of cassette. The detectors 29 and 30 of the cassette 3 allow it to be located immediately using the information sent from the detectors 29 and 30 to the control and processing means 4 via the electrical cable 13. The following truth table is obtained:

|  |  | Identification | |
| --- | --- | --- | --- |
|  |  | Yes | No |
| Insertion | Yes | Puncture System | Breast Support Plate (bucky) |
|  | No | Storage | Transfer Or Unallowed Position |

When the processing and control means 4 receives information output by the insertion detector 29 and information output by the identification detector 30, the cassette 3 is inserted into the housing in the puncture system 2. This is because the puncture system 2 can simultaneously trigger the insertion detector 29 and the identification detector 30.

When the processing and control means 4 receives a signal from the insertion detector 29 and does not receive any signal from the identification detector 30, the cassette 3 is inserted into the breast support plate 6. This is because the breast support plate 6 can cause the mechanical insertion detector 29 to respond but does not have a magnet capable of making the identification detector 30 respond.

When the processing and control means 4 receives a signal from the identification detector 30 and does not receive any signal from the insertion detector 29, the cassette is inserted into the housing in the storage space 17, which does not cause the insertion detector 29 to respond, the said housing being provided with a magnet 31 capable of making the identification detector 30 respond.

When the processing and control means 4 does not receive any signal, either from the insertion detector 29 or from the identification detector 30, the cassette 3 is not inserted into any of the housings intended for it and may be in transit from one to the other or in an unallowed housing. The operator is thus kept permanently informed of the whereabouts of the cassette 3.

The lock 28 of the cassette 3 comprises a locking detector 33 and an analog/digital converter (not represented), which sends a digital signal to the processing and control means 4 when the lock 28 is locked. This may make it possible, for example, to prevent a frame from being taken so long as the cassette 3 is not suitably locked in the housing in the puncture system 2 or in the breast support plate 6. This avoids wasteful emission of X-rays.

Figure 5:
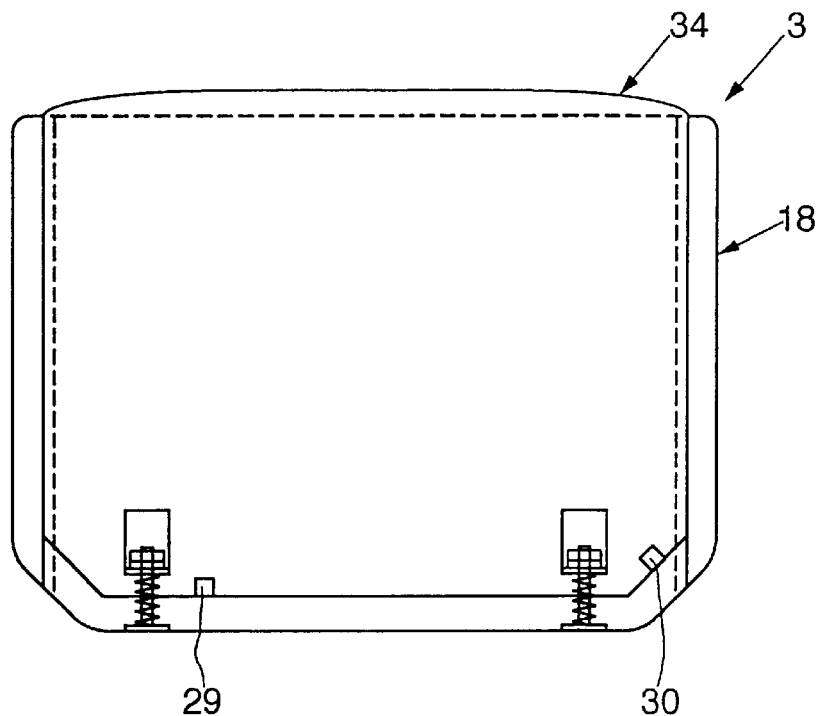
FIGS. 5 and 6 are top views of another embodiment of a cassette.
Figure 6:
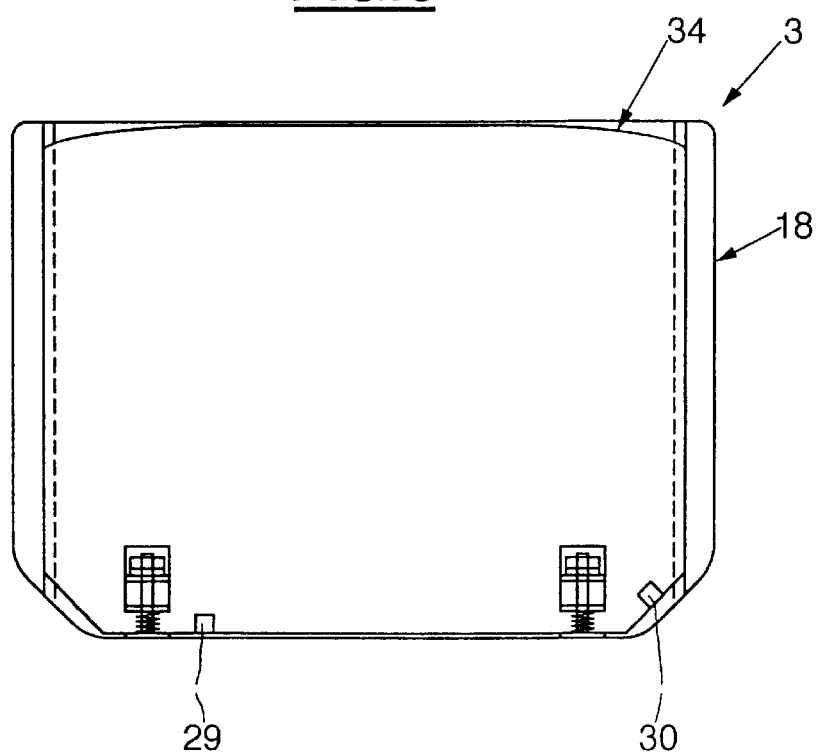

FIGS. 5 and 6 illustrate another embodiment of 30 the invention, in which a cassette 3 comprises a case 18 into which a unit 34 can be slid. This relative motion between the unit 34 and the case 18 makes it possible to separate the sensitive region of the cassette 3, located in the unit 34, from the edge of the case 18 and to reduce the risk of damage due to shock. The insertion detector 29 and the positioning detector 30 may be arranged in the same way as in FIGS. 2 to 4, or could also be arranged on the side edges of the cassette 3. Of course, the detectors 29 and 30 used may be any type of compact detector capable of sending a signal to a processing and control means, for example an electrical contactor instead of a magnetically triggered relay. Furthermore, a sensitive region formed by an array of photodiodes could be used instead of the sensitive region formed by an array of charge-coupled devices.

The invention provides an easily locatable cassette for producing digital images, the storing of which is readily apparent to the operator. This facilitates use of the radiology apparatus.

Various modifications in structure and/or function and/ steps may be made by one skilled in the art without departing from the scope and extent of the invention.

What is claimed is:

1. System for locating a cassette for producing digital images, in a radiography apparatus of the type comprising an X-ray source, means for data processing, a support for the cassette in the active position and a storage space for the cassette in the inactive position, the cassette comprising means for detecting the insertion of the cassette into the support and means for detecting the identification of the cassette.

2. System according to claim 1 comprising means for data processing comprises means for processing the digital signals output by the cassette, and means for controlling the X-ray source.

3. System according to claim 2 comprising means for preventing the introduction of the cassette of standard paraellepipedal format into the storage space, the housing for the cassette in the support and in the storage space being provided with truncated coners and the cassette whose introduction is allowed being of parallelepipedal format with truncated corners.

4. System according to claim 1 comprising means for preventing the introduction of the cassette of standard paraellepipedal format into the storage space, the housing for the cassette in the support and in the storage space being provided with truncated corners and the cassette whose introduction is allowed being of parallelepipedal format with truncated corners.

5. System for locating a cassette for producing digital images comprising a support for the cassette in the active position and a storage space for the cassette in the inactive position, the cassette comprising means for detecting the insertion of the cassette into the support and means for detecting the identification of the cassette.

6. System according to claim 5 having means for data processing comprising means for processing the digital signals output by the cassette, and means for controlling an X-ray source.

7. System according to claim 6 comprising means for preventing the introduction of a cassette having a substantially parallelepipedal format into the storage space, the housing for the cassette in the support and in the storage space being provided with truncated corners, and the cassette whose introduction is allowed being of parallelepipedal format with truncated corners.

8. System according to claim 5 comprising means for preventing the introduction of a cassette having a substantially parallelepipedal format into the storage space, the housing for the cassette in the support and in the storage space being provided with truncated corners, and the cassette whose introduction is allowed being of parallelepipedal format with truncated corners.

9. System according to claim 5 wherein the cassette comprises a detector for detecting insertion into the support.

10. System according to claim 9 wherein the detector is a mechanical relay.

11. System according to claim 5 wherein the cassette comprises a detector for identification in the storage space.

12. System according claim 11 wherein the detector is in the form of a relay magnetically triggered by a magnet fitted to the storage space.

13. System according to claim 5 wherein the cassette comprises a lock for immobilization in the support, a locking detector connected to the support, and means for digitizing the signal from the locking detector in order to send locking data to means for data processing.

14. System according to claim 13 wherein the second support comprises means for preventing the introduction of a cassette having a substantially parallelepipedal format, the housing for the cassette in the second support being provided with truncated coners, and the cassette whose introduction is allowed being of parallelepipedal format with truncated coners.

15. System according to claim 14 wherein the cassette comprises an insertion detector and an identification detector relating to the second support, which are in the form of a mechanical relay and a relay magnetically triggered by a magnet fitted to the second support.

16. System according to claim 14 wherein the cassette comprises a lock for immobilization in the second support, a locking detector connected to the second support, and means for digitizing the signal from the locking detector in order to send locking data to means for data processing.

17. System according claim 13 wherein the cassette comprises a lock for immobilization in the second support, a locking detector connected to the second support, and means for digitizing the signal from the locking detector in order to send locking data to means for data processing.

18. System according to claim 13 wherein the locking detector is an electrical contact.

19. System according to claim 5 comprising a puncture device capable of performing a biopsy and comprising a second support for the cassette in the active position.

20. System according to claim 19 wherein the cassette comprises an insertion detector and an identification detector relating to the second support, which are in the form of a mechanical relay and a relay magnetically triggered by a magnet fitted to the second support.

21. System according to claim 20 wherein the cassette comprises a lock for immobilization in the second support, a locking detector connected to the second support, and means for digitizing the signal from the locking detector in order to send locking data to means for data processing.

22. System according to claim 5 wherein the cassette is equipped with cables for transmission to means for data processing and comprises a handle intended for the cassette to be gripped and for the exit of the cable from the cassette to be protected.

23. System according to claim 5 comprising means for locking the cassette into the support.

* * * * *